US012611142B2

(12) United States Patent
Baba et al.

(10) Patent No.: US 12,611,142 B2
(45) Date of Patent: Apr. 28, 2026

(54) METHOD AND APPARATUS FOR INTRAOPERATIVE NERVE VISUALIZATION USING POLARIZED DIFFUSE REFLECTANCE SPECTROSCOPY AND APPLICATIONS OF SAME

(71) Applicant: VANDERBILT UNIVERSITY, Nashville, TN (US)

(72) Inventors: Justin Baba, Knoxville, TN (US); Anita Mahadevan-Jansen, Nashville, TN (US); Graham Throckmorton, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 149 days.

(21) Appl. No.: 18/094,458

(22) Filed: Jan. 9, 2023

(65) Prior Publication Data
US 2023/0148958 A1 May 18, 2023

Related U.S. Application Data

(62) Division of application No. 16/851,239, filed on Apr. 17, 2020, now abandoned.

(60) Provisional application No. 62/835,562, filed on Apr. 18, 2019.

(51) Int. Cl.
*A61B 5/00* (2006.01)
*A61B 90/30* (2016.01)

(52) U.S. Cl.
CPC .......... *A61B 5/4893* (2013.01); *A61B 5/0075* (2013.01); *A61B 5/0077* (2013.01); *A61B 5/7405* (2013.01); *A61B 5/742* (2013.01);

*A61B 5/7455* (2013.01); *A61B 5/746* (2013.01); *A61B 2090/306* (2016.02); *A61B 2505/05* (2013.01); *A61B 2560/0431* (2013.01); *A61B 2562/0233* (2013.01); *A61B 2576/00* (2013.01)

(58) Field of Classification Search
CPC .................................................... A61B 5/0075
See application file for complete search history.

(56) References Cited

U.S. PATENT DOCUMENTS

| | | | | |
|---|---|---|---|---|
| 6,364,829 | B1 * | 4/2002 | Fulghum | A61B 1/07 600/178 |
| 9,182,280 | B1 * | 11/2015 | Gardner | G01N 21/15 |
| 2001/0033364 | A1 * | 10/2001 | Cabib | G06V 10/88 351/221 |

(Continued)

OTHER PUBLICATIONS

I. Bigio et al, "Diagnosis of breast cancer using elastic-scattering spectroscopy: preliminary clinical results", Journal of Biomedical Optics, vol. 5, No. 2, pp. 221-228, Apr. 2000 (Year: 2000).*

(Continued)

*Primary Examiner* — Nyrobi Celestine
(74) *Attorney, Agent, or Firm* — troutman pepper locke; Tim Tingkang Xia, Esq.

(57) ABSTRACT

An apparatus for intraoperative nerve identification and/or visualization of a target of interest of a living subject comprises a light source; an imaging head configured to acquire a polarized diffuse reflectance spectral image from the illuminated target of interest; and a controller configured to control the imaging head and to process the acquired polarized diffuse reflectance spectral image.

16 Claims, 7 Drawing Sheets

(56)                References Cited

U.S. PATENT DOCUMENTS

| | | | |
|---|---|---|---|
| 2005/0030372 A1* | 2/2005 | Jung | A61B 5/0059 348/77 |
| 2005/0049467 A1* | 3/2005 | Stamatas | A61B 5/445 600/315 |
| 2006/0173359 A1* | 8/2006 | Lin | A61B 18/1477 600/478 |
| 2006/0184040 A1* | 8/2006 | Keller | G01N 21/47 600/476 |
| 2009/0317856 A1* | 12/2009 | Mycek | G01N 21/6408 435/29 |
| 2010/0185064 A1* | 7/2010 | Bandic | A61B 5/444 600/306 |
| 2012/0046554 A1* | 2/2012 | Zelenchuk | A61B 5/4331 600/476 |
| 2013/0296708 A1* | 11/2013 | Zuzak | G01J 3/021 600/476 |
| 2014/0303463 A1* | 10/2014 | Robinson | G01J 3/02 600/316 |
| 2017/0224220 A1* | 8/2017 | Tunnell | G01J 3/02 |
| 2020/0029856 A1* | 1/2020 | Sharareh | A61B 5/0084 |
| 2022/0117476 A1 | 4/2022 | Cha et al. | |
| 2022/0240783 A1* | 8/2022 | Fan | A61B 5/441 |
| 2023/0280577 A1* | 9/2023 | Valdes | G02B 21/361 600/476 |

OTHER PUBLICATIONS

Z. Volynskaya et al, "Diagnosing breast cancer using diffuse reflectance spectroscopy and intrinsic fluorescence spectroscopy", Journal of Biomedical Optics, vol. 13, No. 2, pp. 1-9, Apr. 2008 (Year: 2008).*

L. L. de Boer et al, "Fat/water ratios measured with diffuse reflectance spectroscopy to detect breast tumor boundaries", Breast Cancer Research and Treatment, vol. 152, pp. 509-518, Jul. 2015 (Year: 2015).*

* cited by examiner

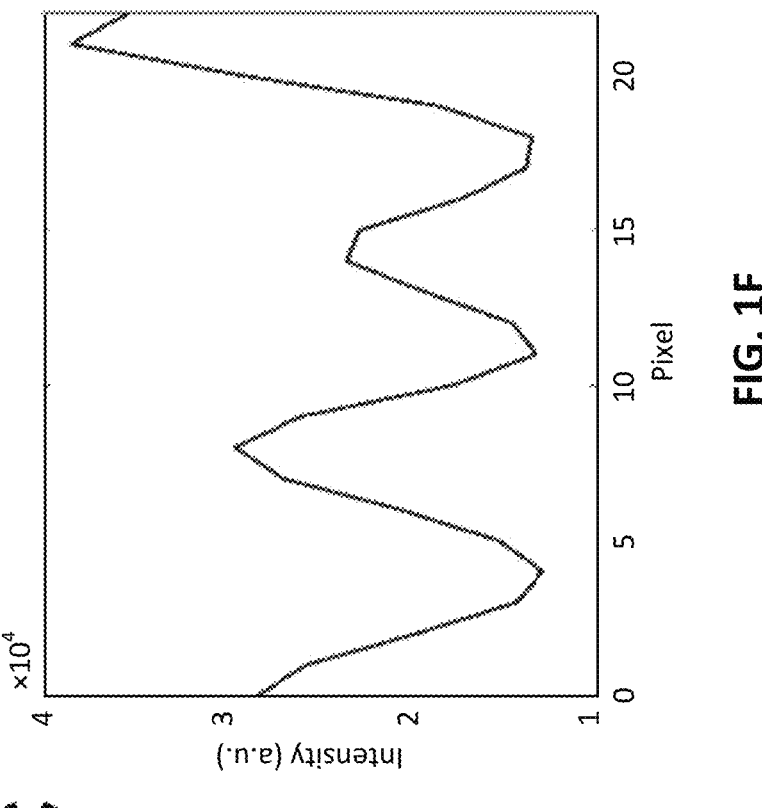
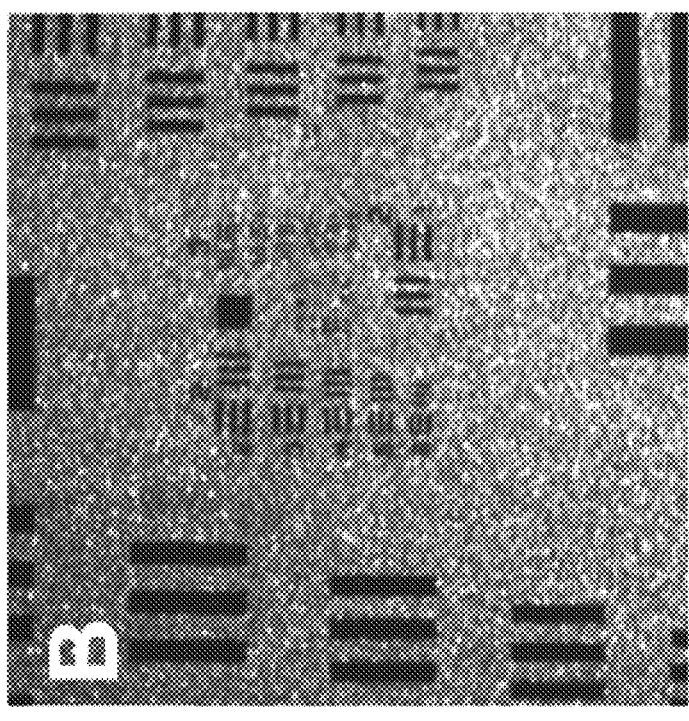
FIG. 1F
FIG. 1E

METHOD AND APPARATUS FOR INTRAOPERATIVE NERVE VISUALIZATION USING POLARIZED DIFFUSE REFLECTANCE SPECTROSCOPY AND APPLICATIONS OF SAME

CROSS-REFERENCE TO RELATED PATENT APPLICATIONS

This application is a divisional application of U.S. patent application Ser. No. 16/851,239, filed Apr. 17, 2020, which itself claims priority to and the benefit of U.S. Provisional Patent Application Ser. No. 62/835,562, filed Apr. 18, 2019, which are incorporated herein by reference in their entireties.

FIELD OF THE INVENTION

The invention relates generally to optical assessments of bio-objects, and more particularly, to method and apparatus for intraoperative nerve visualization using polarized diffuse reflectance spectroscopy, and applications of the same.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

While the central nervous system (CNS) integrates, processes, and coordinates the overall function and activity of the body, the peripheral nervous system (PNS) serves as a highway for the electrical signaling to and from the CNS and the rest of the body. This makes the PNS vital to not only sensation, but also maintaining homeostasis and autonomic functions. In surgery, the preservation of peripheral nerves and their functionality is therefore of the utmost importance. Unfortunately, stretch and crush injuries are not uncommon especially during resections and biopsies. In some cases, these surgeries have a staggering incidence of iatrogenic nerve damage. Two years following a radical prostatectomy nearly 60% of men were impotent as a result of damaged cavernous nerves. Even in surgeries where the risk of neural damage is minimal like acoustic neuroma removal (<1%), spinal scoliosis surgery (<0.6%), and thyroidectomies (<2%), nerve damage can be severe leading to deafness, paraplegia, and even death respectively. Nerve damage is also a common source of medicolegal litigations with compensation being awarded in 82% of cases of spinal accessory nerve injury. For many surgeries, the major factor responsible for lowering the incidence of neural morbidity has been intraoperative neural monitoring (INOM). IONM seeks to preserve nerve function and integrity through monitoring neural activity during surgical procedures. This is primarily achieved through electrical stimulation and electrophysiological recordings which are used to both locate nerves and monitor neural viability. By assessing neural functionality throughout a surgical procedure, the risk of iatrogenic damage is greatly reduced and appropriate measures can be taken if the nerve is damaged. There are, however, innate limitations to INOM. During most nerve sparing procedures, nerves are only intermittently monitored which increases the likelihood of nerve damage in between electrical stimulation events. Thus, immediate corrective action to avoid injury is impossible, and injuries can only be addressed after the fact. Recently, continuous IONM has been employed in thyroidectomies but can yield unreliable EMG signals due to inadvertent electrode dislocation. Moreover, since many INOM techniques involve measuring muscle related phenomena, sensory fibers are unable to be identified and monitored. In a systematic review, nerve stimulation alone failed to localize 20% of peripheral nerves.

Subsequently, a wide variety of methods have been used for intraoperative nerve visualization. Among these are ultrasonography, fluorescence imaging, polarization imaging, and optical coherence tomography (OCT). Each modality, however, has its advantages and short comings. While ultrasonography is real-time, cost-effective, and widely accepted across the medical field, it tends to lack the spatial resolution to visualize smaller nerve branches (<2 mm). Fluorescent imaging improves the resolution and overall contrast between tissues, but it relies on the systemic injection of a fluorescent peptide tag. Moreover, fluorescent tags can be toxic and/or elicit allergic reactions and additionally require FDA approval to be used in clinical trials. Polarization imaging maintains the high spatial resolution of optical techniques but is highly dependent on the orientation of nerve fibers with respect to the polarizers and lacks the contrast of fluorescent imaging. Hence, the efficacy of polarization imaging relies on imaging at the right orientation. Lastly, OCT provides high spatial and temporal resolution 3D reconstructions of imaged tissues. OCT, however, is limited by its imaging depth, intensive image processing, and a small field of view on the order of square millimeters.

Therefore, a heretofore unaddressed need exists in the art to address the aforementioned deficiencies and inadequacies.

SUMMARY OF THE INVENTION

One of the objectives of the invention is to provide a polarized diffuse reflectance spectroscopy (DRS) for intraoperative nerve identification and/or visualization and applications of the same.

In one aspect, the invention relates to an apparatus for intraoperative nerve identification and/or visualization of a target of interest of a living subject. The apparatus comprises a light source; an imaging head configured to acquire a polarized DRS image from the illuminated target of interest; and a controller configured to control the imaging head and to process the acquired polarized DRS image.

In one embodiment, the controller is configured to: cause the imaging head to acquire a background image where the light source does not emit a beam of light; and process the acquired polarized DRS image based on the background image from the polarized DRS images.

In one embodiment, the controller is further configured to: normalize the acquired polarized DRS image based on a normalization spectral marker, wherein the normalization spectral marker corresponds to a wavelength representing one of the least absorbed by the target of interest; and identify a reflectance intensity ratio between the normalization spectral marker and a tissue spectral marker present in the acquired polarized DRS image, wherein the tissue spectral marker corresponds to a wavelength of statistically significant reflectance intensity.

In one embodiment, the normalization spectral marker has a wavelength between about 575 nm to about 700 nm; or the tissue spectral marker has a wavelength between about 410 nm to about 460 nm; or the tissue spectral marker has a wavelength between about 580 nm to about 620 nm.

In one embodiment, the normalization spectral marker has a wavelength between about 680 nm to about 700 nm; or the tissue spectral marker has a wavelength between about 410 nm to about 440 nm; or the tissue spectral marker has a wavelength between about 590 nm to about 610 nm.

In one embodiment, the controller is further configured to: identify a tissue type in the acquired polarized DRS image; and generate a tissue type distribution based on the identified tissue type.

In one embodiment, the controller is further configured to: identify a tissue type in the acquired polarized DRS image; and generate a pixel-by-pixel tissue type distribution based on the identified tissue type.

In one embodiment, the apparatus further comprises a display for displaying and/or projecting the tissue type distribution onto the intraoperative field of view.

In one embodiment, the light source is a broadband light source that emits light at a wavelength of about 100 to about 1200 nm.

In one embodiment, the apparatus further comprises an optical waveguide for directing light emitted from the light source to illuminate the target of interest.

In one embodiment, the optical waveguide comprises: one or more wave plates further comprising a fixed axis of transmission or a variable axis of transmission, or both, wherein the wave plate is configured to produce light with a linear polarization state, an elliptical polarization state, a circular polarization state, or a combination thereof.

In one embodiment, the optical waveguide comprises: one or more optical fibers further comprising at least one of a fixed axis of transmission, a variable axis of transmission, or both, wherein the one or more optical fibers are configured to produce light with a linear polarization state, an elliptical polarization state, a circular polarization state, or combinations thereof.

In one embodiment, the imaging head comprises: a detector disposed in a top portion of the image head for acquiring the DRS images; a tunable filter positioned in a bottom portion of the image head in an optical path for collecting light from the illuminated target of interest; and a lens positioned between the tunable filter and the detector in the optical path for focusing the collected light to the detector.

In one embodiment, the detector comprises at least one camera selected from at least one chargecoupled device (CCD) camera, at least one complementary metal oxide semiconductor (CMOS) camera, at least one photosensor array, at least one infrared camera and/or at least one near-infrared (NIR) camera, or a combination thereof.

In one embodiment, the tunable filter comprises: an optical filter that uses electronically controlled liquid crystal (LC) elements to transmit a selectable wavelength of light and exclude others, with fixed and/or variable polarizations; or a dispersion-based filter configured to produce a spatially distributed continuous wavelength spectrum capable of being operably sampled for individual wavelengths, bands of wavelengths, a full spectrum of wavelengths, or combinations thereof; or variable spectral bandpass filters, variable polarization filters, or a combination thereof.

In one embodiment, the light source is operably modulated by a lock-in scheme or a transistor-transistor logic (TTL) trigger for providing a trigger to sequence and/or initiate data collection for enabling operations of the detector in normal and/or external lighting conditions including room lights.

In one embodiment, the imaging head further comprises one or more lenses positioned between the target of the interest and the tunable filter for focusing the light from the illuminated target of interest to the tunable filter.

In one embodiment, the controller is further configured to provide, based on the processed images, an aural or tactile nerve proximity indication.

In another aspect, the invention relates to an apparatus for intraoperative nerve identification and/or visualization of a target of interest of a living subject. In one embodiment, the apparatus includes a light source for emitting a beam of light to illuminate a target of interest; a light delivering means for delivering the beam of light emitted from the light source onto the target of interest so as to illuminate the target of interest therewith; and an imaging head positioned over the target of interest for acquiring polarized DRS images of light from the illuminated target of interest responsive to the illumination, for identifying and/or visualizing one or more nerves in the target of interest.

In one embodiment, the light source is a broadband light source for emitting the beam of light in a wavelength range of about 100-1200 nm.

In one embodiment, the beam of light emitted from the light source is polarized either inherently or through polarizers with variable axes of transmission delivered to the target of interest.

In one embodiment, the light delivering means comprises one or more fibers and is configured such that light delivered onto the target of interest from at least one of the one or more fibers is unpolarized light; or light delivered onto the target of interest from at least one of the one or more fibers is polarized light having fixed and/or variable polarizations; or light delivered onto the target of interest from one of the one or more fibers is unpolarized light and light delivered onto the target of interest from the others of the one or more fibers is polarized light having fixed and/or variable polarizations.

In one embodiment, the light delivering means comprises one or more lenses configured to deliver the beam of light emitted from the light source onto the target of interest.

In one embodiment, the light delivering means further comprises one or more wave plates configured to polarize the beam of light emitted from the light source as polarized light having fixed and/or variable polarizations.

In one embodiment, the imaging head comprises a detector disposed in a top portion of the image head for acquiring the DRS images; a tunable filter positioned in a bottom portion of the image head in an optical path for collecting light from the illuminated target of interest; and a lens positioned between the tunable filter and the detector in the optical path for focusing the collected light to the detector.

In one embodiment, the detector comprises at least one camera. In one embodiment, the at least one camera comprises at least one CCD camera, at least one CMOS camera, at least one photosensor array, or a combination thereof. In one embodiment, the at least one camera comprises at least one infrared camera and/or at least one NIR camera.

In one embodiment, the tunable filter is an optical filter that uses electronically controlled LC elements to transmit a selectable wavelength of light and exclude others, with fixed and/or variable polarizations. In one embodiment, the LC elements comprise switchable LC wave plates.

In one embodiment, the tunable filter comprises variable spectral bandpass filters, variable polarization filters, or a combination thereof.

In one embodiment, the tunable filter is a spatial grating or other dispersion based optical component that spatially spreads the detected light into continuous wavelength bands for detection by one or more detectors, or a linear detector array, or a two-dimensional (2D) detector array.

In one embodiment, the lens is an adjustable focus lens.

In one embodiment, the light source is operably modulated by a lock-in scheme or a transistor-transistor logic (TTL) trigger for providing a trigger to sequence and/or initiate data collection for enabling operations of the detector in normal and/or external lighting conditions including room lights.

In one embodiment, the imaging head further comprises one or more lenses positioned between the target of the interest and the tunable filter for focusing the light from the illuminated target of interest to the tunable filter.

In one embodiment, the apparatus further comprises a controller configured to coordinately operate the light delivering means to deliver the beam of light onto the target of interest and the image head to acquire the DRS images of the light from the illuminated target of interest, to receive the acquired images from the detector, and to process the acquired images to identify and visualize nerve in the target of interest.

In one embodiment, the controller is further configured to provide, based on the processed images, an aural or tactile nerve proximity indication that allows a surgeon to spatially and manually interrogate locations prior to and/or during execution of tissue surgical manipulations.

In one embodiment, the controller is further configured to provide visual, aural and/or tactile feedbacks including vibration and/or buzzing alerts.

In one embodiment, the apparatus also has a display for displaying the processed images and/or means for projecting the processed images onto the intraoperative field of view.

In yet another aspect, the invention relates to a probe for intraoperative nerve identification and/or visualization of a target of interest of a living subject. In one embodiment, the probe comprises a light delivering means coupled with a light source for delivering a beam of light emitted from the light source onto a target of interest so as to illuminate the target of interest therewith; a light collecting means positioned over the target of interest for collecting light from the illuminated target of interest responsive to the illumination; and an imaging means positioned over the target of interest coupled with the light collecting means for acquiring polarized DRS images of light from the illuminated target of interest responsive to the illumination, for identifying and/or visualizing one or more nerves in the target of interest.

In one embodiment, the light source is a built-in broadband light source or an external broadband light source for emitting the beam of light in a wavelength range of about 100-1200 nm.

In one embodiment, the beam of light emitted from the light source is polarized either inherently or through polarizers with variable axes of transmission delivered to the target of interest.

In one embodiment, the light delivering means comprises one or more fibers and is configured such that light delivered onto the target of interest from at least one of the one or more fibers is unpolarized light; or light delivered onto the target of interest from at least one of the one or more fibers is polarized light having fixed and/or variable polarizations; or light delivered onto the target of interest from one of the one or more fibers is unpolarized light and light delivered onto the target of interest from the others of the one or more fibers is polarized light having fixed and/or variable polarizations.

In one embodiment, the light delivering means comprises one or more lenses configured to deliver the beam of light emitted from the light source onto the target of interest.

In one embodiment, the light delivering means further comprises one or more wave plates configured to polarize the beam of light emitted from the light source in polarized light having fixed and/or variable polarizations.

In one embodiment, the light collecting means comprises a tunable filter for collecting light from the illuminated target of interest; and a lens positioned for focusing the collected light to the imaging means.

In one embodiment, the tunable filter is an optical filter that uses electronically controlled LC elements to transmit a selectable wavelength of light and exclude others, with fixed and/or variable polarizations. In one embodiment, the LC elements comprise switchable LC wave plates.

In one embodiment, the tunable filter comprises variable spectral bandpass filters, variable polarization filters, or a combination thereof.

In one embodiment, the lens is an adjustable focus lens.

In one embodiment, the light source is operably modulated by a lock-in scheme or a TTL trigger for providing a trigger to sequence and/or initiate data collection for enabling operations of the detector in normal and/or external lighting conditions including room lights.

In one embodiment, the light collecting means further comprises one or more lenses positioned between the target of the interest and the tunable filter for focusing the light from the illuminated target of interest to the tunable filter.

In one embodiment, the light collecting means further comprises one or more fibers each having one end coupled to the tunable filter and an opposite, working end operably positioned proximate to the target of interest to collect the light from the illuminated target of interest to the tunable filter.

In one embodiment, the imaging means comprises a detector acquiring the DRS images.

In one embodiment, the detector comprises at least one camera.

In one embodiment, the at least one camera comprises at least one CCD camera, at least one CMOS camera, at least one photosensor array, or a combination thereof. In one embodiment, the at least one camera comprises at least one infrared camera and/or at least one NIR camera.

In one embodiment, the probe also has a controller configured to coordinately operate the light delivering means to deliver the beam of light onto the target of interest, the light collecting means to collect the light from the illuminated target of interest, and the imaging means to acquire the DRS images of the light from the illuminated target of interest, to receive the acquired images from the detector imaging means, and to process the acquired images to identify and visualize nerve in the target of interest.

In one embodiment, the controller is further configured to provide, based on the processed images, an aural or tactile nerve proximity indication that allows a surgeon to spatially and manually interrogate locations prior to and/or during execution of tissue surgical manipulations.

In one embodiment, the controller is further configured to provide visual, aural and/or tactile feedbacks including vibration and/or buzzing alerts.

In one embodiment, the probe further comprises a display for displaying the processed images and/or means for projecting the processed images onto the intraoperative field of view.

In one embodiment, the probe is a handheld probe.

In a further aspect, the invention relates to a method for intraoperative nerve identification and/or visualization of a target of interest of a living subject. In one embodiment, the method include delivering a beam of light onto a target of interest so as to illuminate the target of interest therewith; acquiring polarized DRS images of light from the illuminated target of interest responsive to the illumination; and processing the acquired DRS images to identify and visualize nerve in the target of interest.

In one embodiment, the beam of light delivered onto the target of interest is in a wavelength range of about 100-1200 nm.

In one embodiment, the beam of light delivered onto the target of interest is unpolarized light, polarized light with fixed and/or variable polarizations, or a combination thereof.

In one embodiment, the acquiring step further comprises selectively transmitting a wavelength of the light from the illuminated target of interest; and acquiring a DRS image of the transmitted light; and repeating the transmitting step and the acquiring step over a predetermined wavelength range with a predefined resolution.

In one embodiment, the predetermined wavelength range is from about 200 nm to about 1000 nm, and the predefined resolution is about 1 nm, about nm, about 3 nm, about 4 nm, about 5 nm, or 6 nm.

In one embodiment, the acquiring step further comprises filtering the light from the illuminated target of interest with polarizers so that the light is polarized with fixed and/or variable polarizations.

In one embodiment, the acquiring step comprises acquiring background images without delivering the beam of light onto the target of interest before acquiring images of the illuminated target of interest, and the processing step comprises subtracting the background images from the acquired images of the illuminated target of interest.

In one embodiment, the processing step comprises identifying spectral markers from spectra averaged spectra of the plurality of living subjects for each tissue type, wherein each spectral marker at a wavelength provides a statistically significant difference and biological justification for a corresponding type of tissue, and wherein the averaged spectra for each tissue type are normalized to a peak at about 690 nm, or some other wavelength of significance.

In one embodiment, the processing step further comprises comparing intensity ratios between the wavelengths of the spectral markers and the peak wavelength at about 690 nm, or some other wavelength of significance, to differentiate tissue types; classifying tissues based on thresholds of the intensity ratios; and mapping, using the thresholds, the tissue distribution across the DRS images on a pixel by pixel basis.

In one embodiment, the method further includes displaying the tissue distribution across the DRS images and/or projecting the tissue distribution onto the intraoperative field of view so as to enable intraoperative identification and/or visualization of one or more nerves in the target of interest.

In one embodiment, the method further comprises providing a trigger to sequence and/or initiate data collection for enabling the acquiring operation in normal and/or external lighting conditions including room lights.

In one aspect, the invention relates to non-transitory tangible computer-readable medium storing instructions which, when executed by one or more processors, cause a method for intraoperative nerve identification and/or visualization of a target of interest of a living subject to be performed. The method comprises delivering a beam of light onto a target of interest so as to illuminate the target of interest therewith; acquiring polarized DRS images of light from the illuminated target of interest responsive to the illumination; and processing the acquired DRS images to identify and visualize nerve in the target of interest.

In one embodiment, the acquiring step further comprises selectively transmitting a wavelength of the light from the illuminated target of interest; acquiring a DRS image of the transmitted light; and repeating the transmitting step and the acquiring step over a predetermined wavelength range with a predefined resolution.

In one embodiment, the acquiring step further comprises filtering the light from the illuminated target of interest with polarizers so that the light is polarized with fixed and/or variable polarizations.

In one embodiment, the acquiring step comprises acquiring background images without delivering the beam of light onto the target of interest before acquiring images of the illuminated target of interest, and the processing step comprises subtracting the background images from the acquired images of the illuminated target of interest.

In one embodiment, the processing step comprises identifying spectral markers from spectra averaged spectra of the plurality of living subjects for each tissue type, wherein each spectral marker at a wavelength provides a statistically significant difference and biological justification for a corresponding type of tissue, and wherein the averaged spectra for each tissue type are normalized to a peak at about 690 nm, or some other wavelength of significance.

In one embodiment, the processing step further comprises comparing intensity ratios between the wavelengths of the spectral markers and the peak wavelength at about 690 nm, or some other wavelength of significance, to differentiate tissue types; classifying tissues based on thresholds of the intensity ratios; and mapping, using the thresholds, the tissue distribution across the DRS images on a pixel by pixel basis.

In one embodiment, the method further comprises displaying the tissue distribution across the DRS images and/or projecting the tissue distribution onto the intraoperative field of view so as to enable intraoperative identification and/or visualization of one or more nerves in the target of interest.

In one embodiment, the method further comprises providing a trigger to sequence and/or initiate data collection for enabling the acquiring operation in normal and/or external lighting conditions including room lights.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein. The drawings described below are for illustration purposes only. The drawings are not intended to limit the scope of the present teachings in any way.

FIGS. 1E-1F show system resolution determined to be 150 μm using an Air Force standard.

FIG. 2A: Mean spectra per tissue types (Nerve in blue; Muscle in red; and Fat in green) the standard deviation is plotted in transparent blocks. FIG. 2B: Ratiometric differentiation of nerve from muscle and fat using the 423 nm and 690 nm peak ratio from unnormalized spectra. (** indicates $p<0.01$; * indicates $p<0.05$). FIG. 2C: Ratiometric differentiation of fat and muscle using the 600 nm and 690 nm peak ratio from unnormalized spectra (*** indicates $p<0.001$).

FIG. 3A: DRS image of exposed rat sciatic nerve at 690 nm. FIG. 3B: Tissue distribution maps generated using a peak analysis algorithm. Blue indicates nerve, red indicates muscle, and green indicates fat. Arrow indicates successful identification of about 500 nerve. Boxes indicate areas with high specular reflectance.

DETAILED DESCRIPTION OF THE INVENTION

Figure 1A:
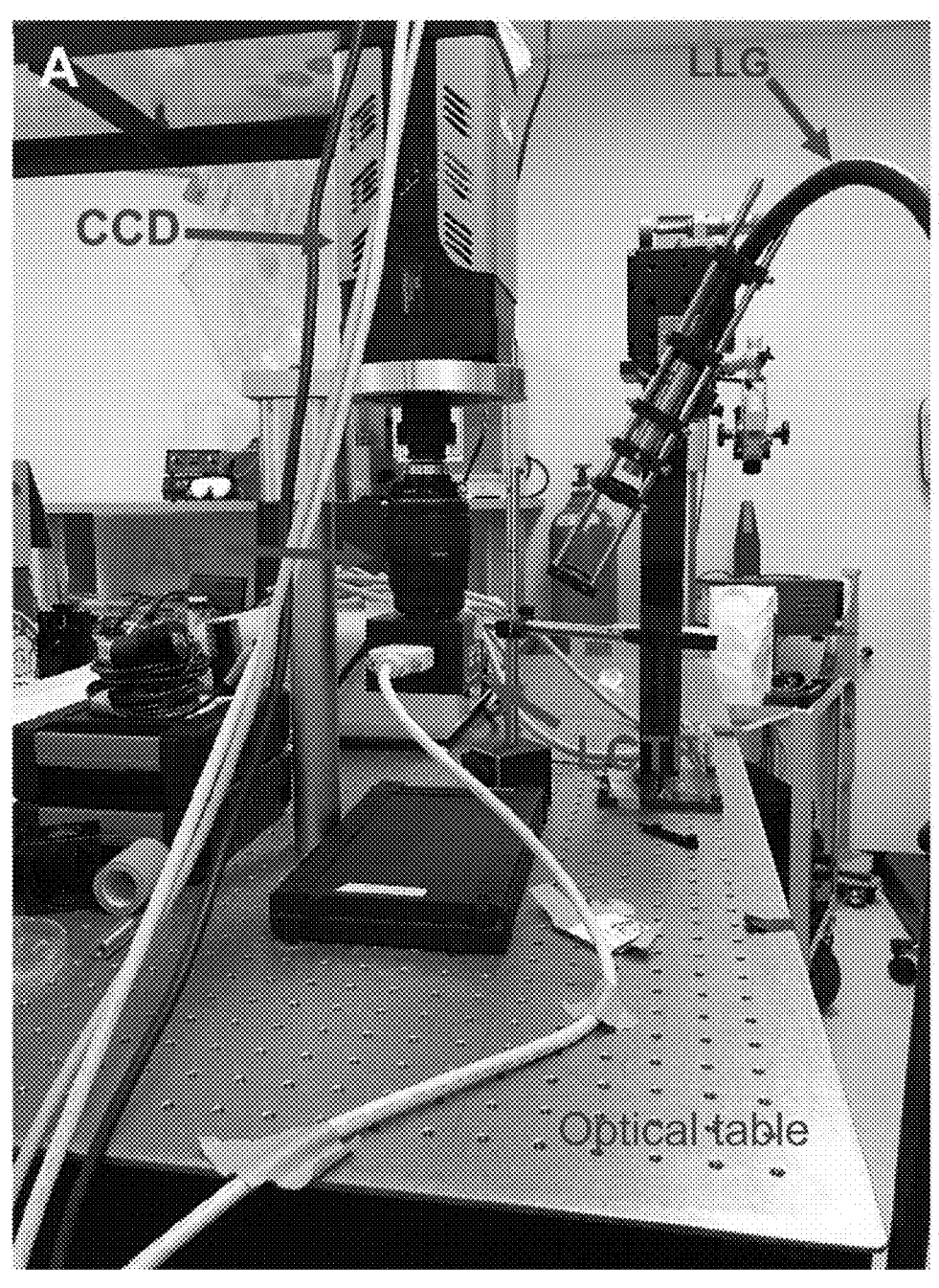
FIG. 1A shows an optical set-up of a liquid crystal tunable filter (LCTF) spectral imaging system with a liquid light guide (LLG), an LCTF, an adjustable focus lens (AF), and CCD, and a controller, according to one embodiment of the invention.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that, as used in the description herein and throughout the claims that follow, the meaning of "a", "an", and "the" includes plural reference unless the context clearly dictates otherwise. Also, it will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in this disclosure, the phrase "at least one of A, B, and C" should be construed to mean a logical (A or B or C), using a non-exclusive logical OR. As used herein, the term "and/or" includes any and all combinations of one or more of the associated listed items.

As used in this disclosure, the term "living subject" refers to a human being such as a patient, or a mammal animal such as a monkey.

As used in this disclosure, the term "diffuse reflectance spectroscopy" refers to a technique for studying spectral characteristics of a target of interest, based on diffuse reflection that arises from the interaction of light with various chemical and physical factors within the target of interest. These interactions include the absorption, transmission, and scattering properties of the illuminated target of interest.

A liquid crystal tunable filter (LCTF) is an optical filter that uses electronically controlled liquid crystal (LC) elements to transmit a selectable wavelength of light and exclude others. The LC elements include, but are not limited to, switchable LC wave plates.

As used in this disclosure, "charge-coupled device" or "CCD" refers to an analog shift register that enables the transportation of analog signals (electric charges) through successive stages (capacitors), controlled by a clock signal. Charge-coupled devices can be used as a form of memory or for delaying samples of analog signals. Today, they are most widely used in arrays of photoelectric light sensors to serialize parallel analog signals. In a CCD for capturing images, there is a photoactive region (an epitaxial layer of silicon), and a transmission region made out of a shift register (the CCD, properly speaking). An image is projected through a lens onto the capacitor array (the photoactive region), causing each capacitor to accumulate an electric charge proportional to the light intensity at that location. A one-dimensional array, used in line-scan cameras, captures a single slice of the image, while a two-dimensional array, used in video and still cameras, captures a two-dimensional picture corresponding to the scene projected onto the focal plane of the sensor. Once the array has been exposed to the image, a control circuit causes each capacitor to transfer its contents to its neighbor (operating as a shift register). The last capacitor in the array dumps its charge into a charge amplifier, which converts the charge into a voltage. By repeating this process, the controlling circuit converts the entire semiconductor contents of the array to a sequence of voltages, which it samples, digitizes and stores in some form of memory.

Embodiments of the invention are illustrated in detail hereinafter with reference to accompanying drawings. The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

A wide range of surgical procedures require working in areas containing important nerve and neural structures. As a result, intraoperative nerve injury is a prevalent surgical risk and common source of medicolegal litigation. Currently, surgeons rely on their anatomical knowledge and naked-eye visualization of the surgical field to identify nerves. This can lead to nerve injury in up to 60% of some cases even with the aid of intraoperative nerve monitoring which is only intermittently applied.

To address the aforementioned deficiencies and inadequacies, the invention in one aspect discloses apparatuses and methods for label-free identification and visualization of peripheral nerves using polarization imaging (PI) and DRS. This invention allows for non-contact, real-time visualization of nerves within the surgical field. PI and DRS rely solely on the innate optical properties of the nerve and surrounding tissue for contrast eliminating the need for the administration of exogenous contrast agents. In this way, surgeons are able to actively avoid damaging vital nerves or neural structures in real-time without contact with or alteration of the surgical site. DRS non-invasively detects changes in optical absorption and scattering within tissue that can be used to discriminate tissue types. PI provides another label-free and complementary means to optically identify nerves based on polarized light's sensitivity to the orderly structure of myelination sheath. Together these two optical modalities can provide high-fidelity, label-free, and non-contact identification and visualization of nerves within a surgical field. Using ratio-metric comparison of spectral tissue markers combined with polarization data, nerves are distinguished and located on a pixel by pixel basis. Nerve visualization can be communicated to the surgeon either through displays or projections onto the surgical field. It should be appreciated to one skilled in the art that the apparatus and method disclosed herein are not limited to just identifying and/or visualizing nerves, but can be applied in other instances connective tissue, fat, muscle, blood vessels, etc., as well.

To the inventors' knowledge, combination of the two imaging modalities, PI and DRS, into one clinical instrument according to the invention has not yet been reported at the time when the invention was made.

In one aspect, this invention relates to a system/apparatus/probe for label-free identification and visualization of peripheral nerves and/or other targeted tissue species of interest in the surgical field, such as nerve, muscle, tendon (connective), vascular, adipose tissues, and so on, using DRS and PI. DRS non-invasively detects changes in optical absorption and scattering within tissue that can be used to discriminate tissue types. PI provides another label-free and complementary means to optically identify nerves based on polarized light's sensitivity to the orderly structure of myelination sheath. Together these two optical modalities can provide high-fidelity, label-free, and non-contact identification and visualization of nerves within a surgical field.

For DRS, this system utilizes a light source that is coupled into a liquid light guide that, in turn, delivers light emitted from the light source onto the surgical field. Alternate forms of the light deliver include fiber optics or a series of lens. Once the light has been delivered to and interacted with the tissue, reflected and back-scattered light is then collected, passed through variable spectral bandpass filters to acquire hyperspectral images, and imaged onto a camera or photodiode, or photodiode array.

PI can be acquired separately from or simultaneously with the DRS hyperspectral images. The PI utilizes a light source whose output is polarized either inherently or through polarizers with variable axes of transmission delivered to the surgical field. These polarizers are capable of selecting or producing light with linear, elliptical, and circular polarization states. Reflected or back-scattered light is then collected from the tissue, passed through another set polarizers, and imaged onto a CCD or photodiode. Similarly, these polarizers are capable of selecting or producing light with linear, elliptical, and circular polarization states.

Using ratio-metric comparison of spectral tissue markers combined with polarization data, nerves are distinguished and located on a pixel by pixel basis. In this way, the nerve identification is partially determined by the spatial resolution of the system meaning it can be modified for microsurgeries or surgeries with large surgical fields. Moreover, tissue discrimination can be done periodically or in real-time depending on the surgeons' preference. Nerve visualization can be communicated to the surgeon either through displays or projections onto the surgical field.

In certain embodiments, the system combining polarization and diffuse reflectance spectroscopy can be used in vivo for tissue discrimination of nerve(s) in a rat leg model. Data analysis methods are disclosed and spectral markers are identified. All various avenues to display nerve visualization (displaying on a monitor, projection onto surgical field, etc.) are explored.

In certain embodiments, some ex vivo experiments are conducted using diffuse reflectance alone for tissue discrimination (nerve, fat, and muscle) and nerve visualization.

Figures 1B, 1C, 1D:
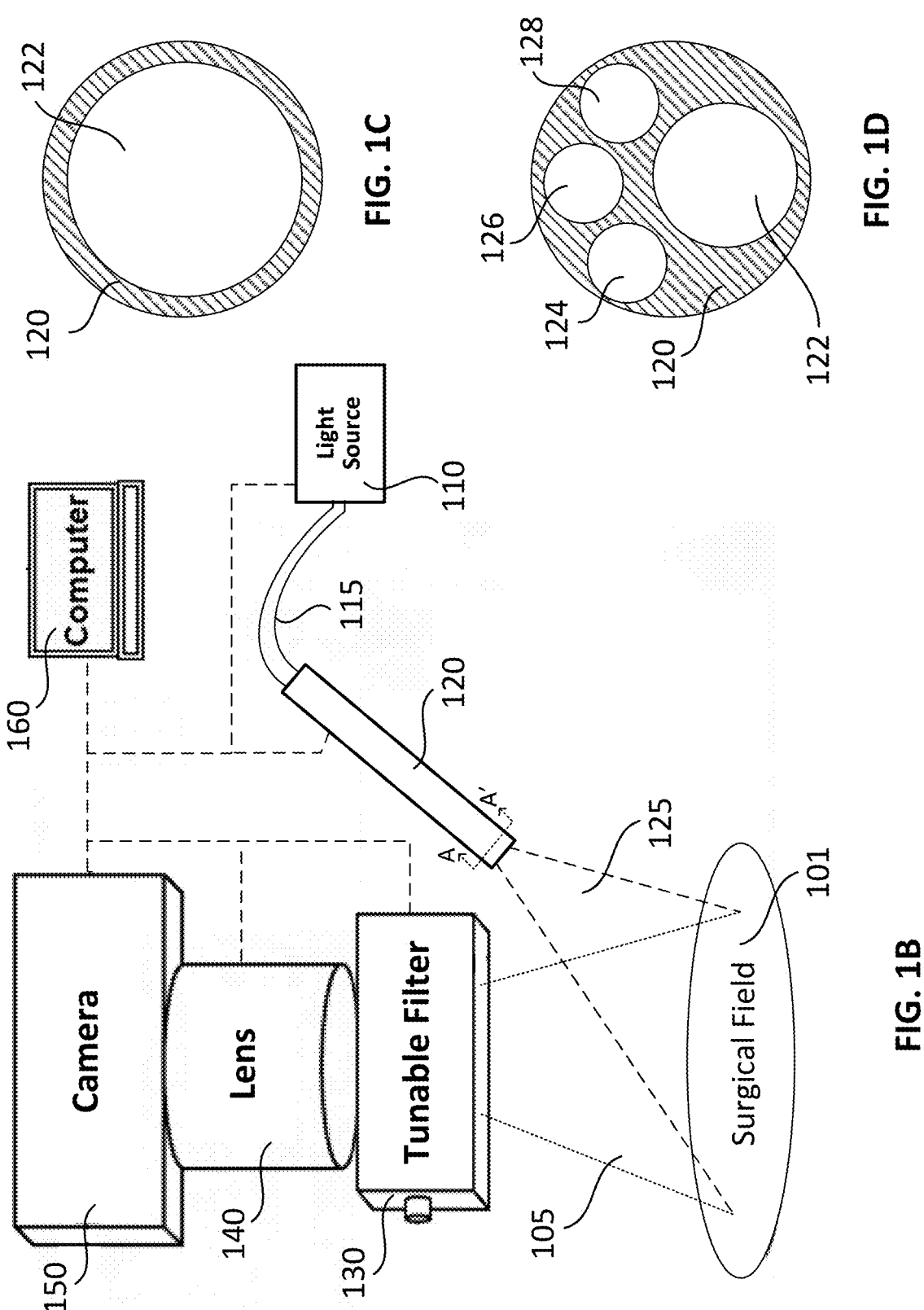
FIG. 1B shows schematically an apparatus for intraoperative nerve visualization using polarized diffuse reflectance spectroscopy, according to one embodiment of the invention.
FIGS. 1C-1D shows schematically two embodiments of a light delivering means according to the invention.

Referring to FIGS. 1A-1D, and particularly to FIG. 1B, an apparatus for intraoperative nerve identification and/or visualization of a target of interest of a living subject is shown according to one embodiment of the invention. In the exemplary embodiment, the apparatus includes a light source 110 for emitting a beam of light to illuminate a target of interest 101, and a light delivering means 120 coupled with the light source 110 via a liquid light guide (LLG) 115 for delivering the beam of light emitted from the light source 110 onto the target of interest 101 so as to illuminate the target of interest 101 therewith. The light delivering means 120 can be coupled with the light source 110 via other optical means such as fibers, or lenses. The target of interest 101 can be a surgical field or site.

In one embodiment, the light source 110 is a broadband light source for emitting the beam of light in a wavelength range of about 100-1200 nm. The beam of light emitted from the light source is polarized either inherently or through polarizers with variable axes of transmission delivered to the target of interest.

In one embodiment, the light delivering means 120 comprises one or more fibers, as shown in FIGS. 1C and 1D, where the former indicates the light delivering means 120 has one fiber 122, while the latter shows the light delivering means 120 has four fibers 122, 124, 126 and 128. The light delivering means 120 is configured such that (a) light 125 delivered onto the target of interest 101 from the one or more fibers is unpolarized light; or (b) light 125 delivered onto the target of interest 101 from the one or more fibers is polarized light having fixed and/or variable polarizations; or (c) light 125 delivered onto the target of interest 101 from one (e.g., fiber 122) of the one or more fibers is unpolarized light and light 125 delivered onto the target of interest 101 from the others (e.g., fibers 124, 126 and 128) of the one or more fibers is polarized light having fixed and/or variable polarizations.

If the beam of light emitted from the light source is not polarized, the light delivering means 120 may have one or more wave plates, or polarizers, to covert the beam of light in polarized light having fixed and/or variable polarizations.

In one embodiment, the light delivering means 120 may comprise one or more lenses configured to deliver the beam of light emitted from the light source 110 onto the target of interest 101.

Back to FIG. 1B now, the apparatus also includes an imaging head positioned over the target of interest 101 for acquiring polarized DRS images of light 105 reflected and backscattered from the illuminated target of interest 101 responsive to the illumination 125, for identifying and/or visualizing one or more nerves in the target of interest. The imaging head comprises a detector 150 disposed in a top portion of the image head for acquiring the DRS images; a tunable filter 130 positioned in a bottom portion of the image head in an optical path for collecting the light 105 from the illuminated target of interest; and a lens 140 positioned between the tunable filter 130 and the detector 150 in the optical path for focusing the collected light to the detector 150.

In one embodiment, the detector 150 comprises at least one camera. In one embodiment, the at least one camera comprises at least one CCD camera, at least one CMOS camera, at least one photosensor array, or a combination thereof. In one embodiment, the at least one camera comprises at least one infrared camera and/or at least one NIR camera.

In one embodiment, the tunable filter 130 is an optical filter that uses electronically controlled LC elements to transmit a selectable wavelength of light and exclude others, with fixed and/or variable polarizations. In one embodiment, the LC elements comprise switchable LC wave plates.

In one embodiment, the tunable filter 130 may comprise variable spectral bandpass filters, variable polarization filters, or a combination thereof.

In one embodiment, the tunable filter 130 is a dispersion based filter that produces a spatially distributed continuous wavelength spectrum that can be sampled for wavelengths including selecting wavelengths, not restricted to individual but also extending to a selection of a full wavelength spread spectrum.

In one embodiment, the lens 140 is an adjustable focus lens.

In one embodiment, the light source is operably modulated by a lock-in scheme or a TTL trigger for providing a trigger to sequence and/or initiate data collection for enabling operations of the detector in normal and/or external lighting conditions including room lights. In one embodiment, the imaging head further comprises one or more lenses (not shown) positioned between the target of the interest 101 and the tunable filter 130 for focusing the light 105 from the illuminated target of interest 101 to the tunable filter 130.

In addition, the apparatus further comprises a controller 160 configured to coordinately operate the light delivering means 120 to deliver the beam of light onto the target of interest 101 and the image head to acquire the DRS images of the light from the illuminated target of interest, to receive the acquired images from the detector 150, and to process the acquired images to identify and visualize nerve in the target of interest.

In one embodiment, the controller 160 is configured to: cause the imaging head to acquire a background image where the light source does not emit a beam of light; and process the acquired polarized DRS image based on the background image from the polarized DRS images.

In one embodiment, the controller 160 is further configured to: normalize the acquired polarized DRS image based on a normalization spectral marker, wherein the normalization spectral marker corresponds to a wavelength representing one of the least absorbed by the target of interest; and identify a reflectance intensity ratio between the normalization spectral marker and a tissue spectral marker present in the acquired polarized DRS image, wherein the tissue spectral marker corresponds to a wavelength of statistically significant reflectance intensity.

In one embodiment, the normalization spectral marker has a wavelength between about 575 nm to about 700 nm; or the tissue spectral marker has a wavelength between about 410 nm to about 460 nm; or the tissue spectral marker has a wavelength between about 580 nm to about 620 nm.

In one embodiment, the normalization spectral marker has a wavelength between about 680 nm to about 700 nm; or the tissue spectral marker has a wavelength between about 410 nm to about 440 nm; or the tissue spectral marker has a wavelength between about 590 nm to about 610 nm.

In one embodiment, the controller 160 is further configured to: identify a tissue type in the acquired polarized DRS image; and generate a tissue type distribution based on the identified tissue type.

In one embodiment, the controller 160 is further configured to: identify a tissue type in the acquired polarized DRS image; and generate a pixel-by-pixel tissue type distribution based on the identified tissue type.

In one embodiment, the controller 160 is further configured to provide, based on the processed images, an aural or tactile nerve proximity indication.

In one embodiment, the controller 160 is further configured to provide, based on the processed images, an aural or tactile nerve proximity indication that allows a surgeon to spatially and manually interrogate locations prior to and/or during execution of tissue surgical manipulations.

In one embodiment, the controller 160 is further configured to provide visual, aural and/or tactile feedbacks including vibration and/or buzzing alerts.

In one embodiment, the apparatus also has a display (e.g., a part of 160) for displaying the processed images. Further, the apparatus may also have means for projecting maps of the tissue distribution onto the intraoperative field of view. For example, the maps can be projected onto the surgeons' field of view by incorporating into their surgical loupe, microscope, glasses, goggles, or on an external screen.

Another aspect of the invention relates to a probe for intraoperative nerve identification and/or visualization of a target of interest of a living subject. The probe comprises a light delivering means coupled with a light source for delivering a beam of light emitted from the light source onto a target of interest so as to illuminate the target of interest therewith; a light collecting means positioned over the target of interest for collecting light from the illuminated target of interest responsive to the illumination; and an imaging means positioned over the target of interest coupled with the light collecting means for acquiring polarized DRS images of light from the illuminated target of interest responsive to the illumination, for identifying and/or visualizing one or more nerves in the target of interest.

In one embodiment, the light source is a built-in broadband light source or an external broadband light source for emitting the beam of light in a wavelength range of about 100-1200 nm.

In one embodiment, the beam of light emitted from the light source is polarized either inherently or through polarizers with variable axes of transmission delivered to the target of interest.

In one embodiment, the light delivering means comprises one or more fibers and is configured such that light delivered onto the target of interest from at least one of the one or more fibers is unpolarized light; or light delivered onto the target of interest from at least one of the one or more fibers is polarized light having fixed and/or variable polarizations; or light delivered onto the target of interest from one of the one or more fibers is unpolarized light and light delivered onto the target of interest from the others of the one or more fibers is polarized light having fixed and/or variable polarizations.

In one embodiment, the light delivering means comprises one or more lenses configured to deliver the beam of light emitted from the light source onto the target of interest.

In one embodiment, the light delivering means further comprises one or more wave plates configured to polarize the beam of light emitted from the light source in polarized light having fixed and/or variable polarizations.

In one embodiment, the light collecting means comprises a tunable filter for collecting light from the illuminated target of interest; and a lens positioned for focusing the collected light to the imaging means.

In one embodiment, the tunable filter is an optical filter that uses electronically controlled LC elements to transmit a selectable wavelength of light and exclude others, with fixed and/or variable polarizations. In one embodiment, the LC elements comprise switchable LC wave plates.

In one embodiment, the tunable filter comprises variable spectral bandpass filters, variable polarization filters, or a combination thereof.

In one embodiment, the tunable filter is a dispersion based filter that produces a spatially distributed continuous wavelength spectrum that can be sampled for wavelengths including selecting wavelengths, not restricted to individual but also extending to a selection of a full wavelength spread spectrum.

In one embodiment, the lens is an adjustable focus lens.

In one embodiment, the light source is operably modulated by a lock-in scheme or a TTL trigger for providing a trigger to sequence and/or initiate data collection for enabling operations of the detector in normal and/or external lighting conditions including room lights.

In one embodiment, the light collecting means further comprises one or more lenses positioned between the target of the interest and the tunable filter for focusing the light from the illuminated target of interest to the tunable filter.

In one embodiment, the light collecting means further comprises one or more fibers each having one end coupled to the tunable filter and an opposite, working end operably positioned proximate to the target of interest to collect the light from the illuminated target of interest to the tunable filter.

In one embodiment, the imaging means comprises a detector acquiring the DRS images.

In one embodiment, the detector comprises at least one camera.

In one embodiment, the at least one camera comprises at least one CCD camera, at least one CMOS camera, at least one photosensor array, or a combination thereof. In one embodiment, the at least one camera comprises at least one infrared camera and/or at least one NIR camera.

In one embodiment, the probe also has a controller configured to coordinately operate the light delivering means to deliver the beam of light onto the target of interest, the light collecting means to collect the light from the illuminated target of interest, and the imaging means to acquire the DRS images of the light from the illuminated target of interest, to receive the acquired images from the detector imaging means, and to process the acquired images to identify and visualize nerve in the target of interest.

In one embodiment, the controller is further configured to provide, based on the processed images, an aural or tactile nerve proximity indication that allows a surgeon to spatially and manually interrogate locations prior to and/or during execution of tissue surgical manipulations.

In one embodiment, the controller is further configured to provide visual, aural and/or tactile feedbacks including vibration and/or buzzing alerts.

In one embodiment, the probe further comprises a display for displaying the processed images and/or means for projecting the maps of processed tissue distribution onto the intraoperative field of view. In certain embodiments, the projecting means can be, but are not limited to, surgical loupe, microscope, glasses, goggles, or projector.

In one embodiment, the probe is a handheld probe.

Yet another aspect of the invention relates to a method for intraoperative nerve identification and/or visualization within a target of interest of a living subject.

In one embodiment, the method include delivering a beam of light onto a target of interest so as to illuminate the target of interest therewith; acquiring polarized DRS images of light from the illuminated target of interest responsive to the illumination; and processing the acquired DRS images to identify and visualize nerve in the target of interest.

In one embodiment, the beam of light delivered onto the target of interest is in a wavelength range of about 100-1200 nm.

In one embodiment, the beam of light delivered onto the target of interest is unpolarized light, polarized light with fixed and/or variable polarizations, or a combination thereof.

In one embodiment, the acquiring step further comprises selectively transmitting a wavelength of the light from the illuminated target of interest; and acquiring a DRS image of the transmitted light; and repeating the transmitting step and the acquiring step over a predetermined wavelength range with a predefined resolution.

In one embodiment, the predetermined wavelength range is from about 200 nm to about 1000 nm, and the predefined resolution is about 1 nm, about 2 nm, about 3 nm, about 4 nm, about 5 nm, or 6 nm.

In one embodiment, the acquiring step further comprises filtering the light from the illuminated target of interest with polarizers so that the light is polarized with fixed and/or variable polarizations.

In one embodiment, the acquiring step comprises acquiring background images without delivering the beam of light onto the target of interest before acquiring images of the illuminated target of interest, and the processing step comprises subtracting the background images from the acquired images of the illuminated target of interest.

In one embodiment, the processing step comprises identifying spectral markers from spectra averaged from the spectra of the plurality of living subjects for each tissue type, wherein each spectral marker at a wavelength provides a statistically significant difference and biological justification for a corresponding type of tissue, and wherein the averaged spectra for each tissue type are normalized to a peak at about 690 nm, or some other wavelength of significance.

In one embodiment, the processing step further comprises comparing intensity ratios between the wavelengths of the spectral markers and the peak wavelength at about 690 nm, or some other wavelength of significance, to differentiate tissue types; classifying tissues based on thresholds of the intensity ratios; and mapping, using the thresholds, the tissue distribution across the DRS images on a pixel by pixel basis.

In one embodiment, the method further includes displaying the tissue distribution across the DRS images and/or projecting the tissue distribution onto the intraoperative field of view so as to enable intraoperative identification and/or visualization of one or more nerves in the target of interest. In one embodiment, the method further includes providing a trigger to sequence and/or initiate data collection for enabling the acquiring operation in normal and/or external lighting conditions including room lights.

It should be noted that all or a part of the steps according to the embodiments of the present invention is implemented by hardware or a program instructing relevant hardware. Yet another aspect of the invention provides a non-transitory tangible computer-readable medium storing instructions which, when executed by one or more processors, cause the apparatus or probe to perform the above method for intraoperative nerve identification and/or visualization of a target of interest of a living subject. The computer executable instructions or program codes enable a computer or a similar computing system to complete various operations in the above disclosed method for privilege management. The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

Traditionally, surgeons rely on their training and anatomical knowledge to avoid damaging nerves within the field of surgery. Recently, nerves have been imaged preoperatively using Mill, diffusion tensor imaging, and ultrasonography to prepare for the procedure. Early diagnosis is then largely dependent on the surgeons' awareness of the injury and its symptoms. Recently, intraoperative neural monitoring (IONM) has lowered the incidence of neural morbidity. The IONM seeks to preserve nerve function and integrity through monitoring neural activity during surgical procedures. This is primarily achieved through electrical stimulation (ES) and electrophysiological recordings which are used to both locate nerves and monitor neural viability. By assessing neural functionality throughout a surgical procedure, the risk of iatrogenic damage is greatly reduced and appropriate measures can be taken if the nerve is damaged. Some commercial systems such as Nerveana® and the NIM® system are manually controlled by the surgeon during thyroidectomies while others like the PropPrep® Nerve Monitoring System can be used during robotic prostatectomies. Despite improving patient outcomes, the IONM methodologies have innate limitations.

During most nerve sparing procedures, nerves are only intermittently monitored which increases the likelihood of nerve damage in between ES events. Thus, immediate corrective action to avoid injury is impossible, and injuries can only be addressed after the fact. Recently, continuous IONM has been employed in thyroidectomies but can yield unreliable EMG signals due to inadvertent electrode dislocation. ES remains prone to current spread as unconfined charge is distributed throughout the adjacent tissue. As a result, ES excites multiple neurons leading to a population response of all neural tissue within close proximity to the electrode. This leads to poor spatial specificity and resolution during nerve identification and mapping. In surgeries like radical prostatectomy and acoustic neuroma removal, ES's poor spatial resolution can prevent the maximal excision of diseased tissue in an effort to maintain nerve function.

Unlike IONM, the apparatus and probe according to embodiments of the invention provides a real-time feedback of the current location of nerves within the surgical field rather than intermittent evaluations. Moreover, nerve mapping does not depend on ES, and therefore, is not be limited by the current spread of ES but by the optical resolution of the system. The system according to embodiments of the invention also provides an image to guide surgeons instantaneously rather than manually probing the surgical site with an electrode searching for nerves. This helps reduce operation time. Lastly, the apparatus and probe according to embodiments of the invention does not require contact with the tissue eliminating the risk of erroneous results from improper electrode contact.

These and other aspects of the present invention are further described below. Without intent to limit the scope of the invention, examples according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

EXAMPLE

Rat Peripheral Nerve Identification Using Diffuse Reflectance Spectroscopy

A wide range of surgical procedures require working in areas containing important nerve and neural structures. As a result, intraoperative nerve injury is a prevalent surgical risk and source of medicolegal litigations. Currently, surgeons rely on their anatomical knowledge and visualization of the surgical field to identify nerves which, in some cases, can lead to nerve injury in up to 60% of some cases even with the aid of intraoperative nerve monitoring.

In this non-limiting exemplary example, the label-free identification of peripheral nerves using DRS is demonstrated. DRS noninvasively detects changes in optical absorption and scattering within tissue that are used to classify tissue. DRS measurements were performed on exposed rat sciatic nerves with small nerve branches (<1 mm in diameter), and spectral markers were identified for nerve, muscle, and adipose tissue. Nerve tissue was distinguished using an enhanced peak located at about 423 nm. Muscle and adipose tissue were differentiated using the differences in reflectance at about 600 nm owing to brown adipose tissue. Images of the tissue distribution were then generated using the spectral markers and were able to successfully identify submillimeter diameter nerves. These results indicate that DRS is a potentially valuable technique for intraoperative nerve localization.

DRS is an optical spectroscopy in which a target of interest, e.g., a bio-object such as tissue, is exposed to a range of wavelengths and the specularly and diffusely reflected light is collected. Since DRS involves collecting backscattered light that has entered the tissue, DRS depends on the intrinsic optical properties of the tissue and can be used to back-calculate these properties without the need of exogenous labels. Additionally, the innate differences in optical properties between tissue types also allows DRS to distinguish tissues such as colon polyps, skin melanomas, oral cancer, and gliomas from healthy surrounding tissue in vivo. In the present example, DRS was used to characterize nerve, adipose, and skeletal muscle in a rat model. Spectra were analyzed and used to identify statistically significant spectral differences between each tissue. Images of the tissue distribution were then generated based on the DRS markers. The results provide a proof-of-concept demonstration of DRS' capability to intraoperatively detect and distinguish nerves.

Materials and Methods

Animal Studies: All animal experiments were conducted at the Vanderbilt University W.M. Keck Free Electron Laser Center and the Vanderbilt Biophotonics Center. DRS measurements were made on euthanized Spraque-Dawley rats used in other experiments in accordance with the National Institute of Health Guide for the Care and Use of Laboratory Animals (n=6). During the surgery, an incision was made posterior-laterally from the pelvic cavity to the knee to expose the sciatic nerve. Once exposed, the epineurium was removed as part of the preceding experiment's protocol. Rats were then placed in a prone position and imaged.

Figure 1G:
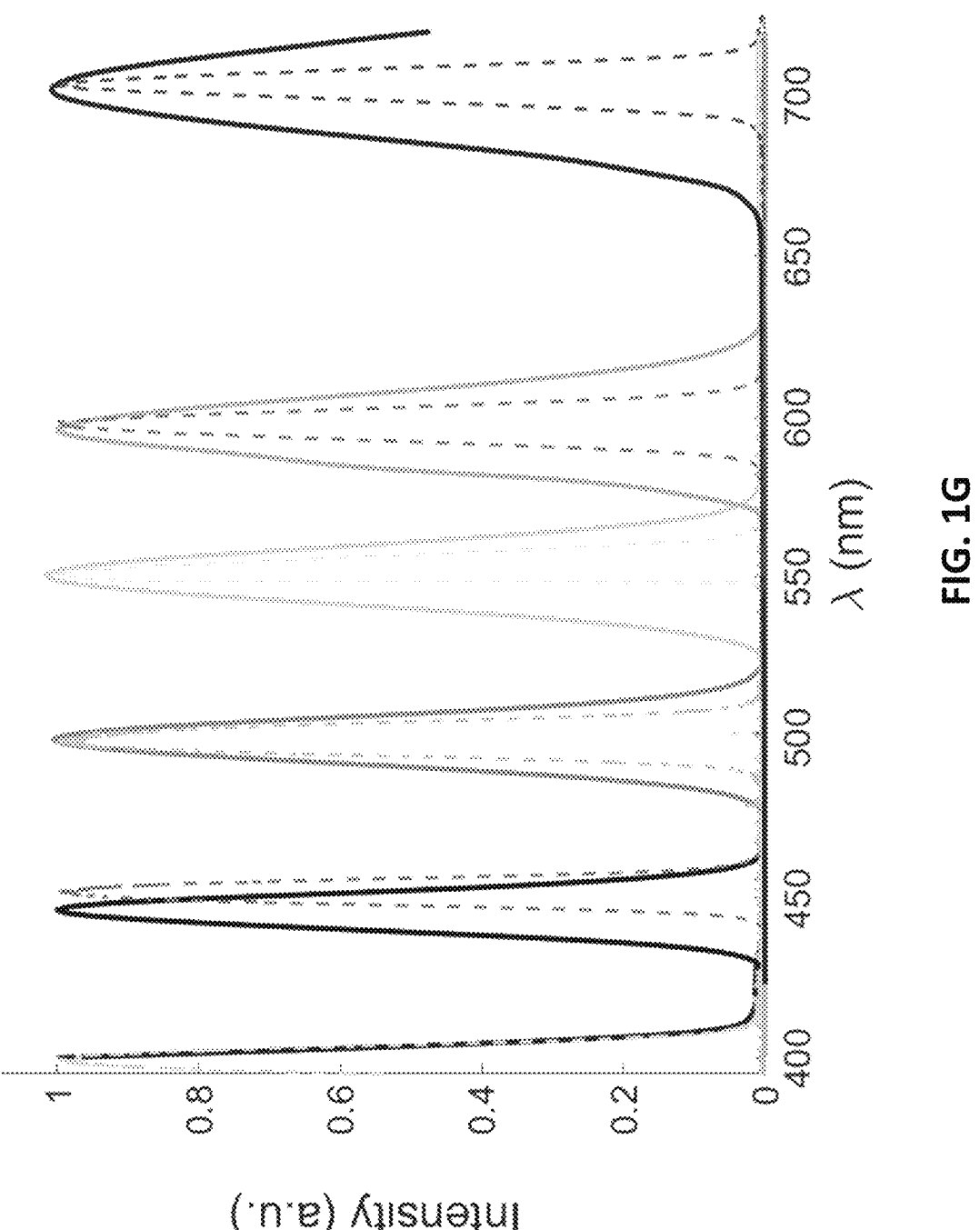
FIG. 1G shows spectral characterization/accuracy according to one embodiment of the invention. Solid lines indicate spectra measured with the LCTF spectral imaging system while dashed are the spectra measured with an Ocean Optics USB spectrometer.

Diffuse Reflectance Spectroscopy: An about 200 W halogen lamp (Luxtec) was used as the white light source for DRS. As shown in FIGS. 1A-1B, light was delivered to the surgical site via an about 10 mm liquid light guide (LLG, Steiner and Martins) and collected using variable focal (f=28-80 mm) length camera lens (AF, Nikon) and imaged onto a 512×512 pixel CCD camera (PhotonMax, Princeton Instruments) through a liquid crystal tunable filter (LCTF, Varispec VIS-20, CRI, Inc.) to acquire spectral images. The CCD camera was mounted onto an arm perpendicular to an optical table. The output of the liquid fiber was collimated and evenly illuminated the surgical site. The resolution of the system was determined to be about 150 μm using a peak to valley ratio threshold equal to the square root of two, as shown in FIGS. 1E-1F. Spectral characterization was performed for the LCTF spectral imaging system using narrow bandpass optical filters to assess its accuracy, as shown in FIG. 1G. LCTF measurements were then confirmed with an Ocean Optics USB spectrometer.

All DRS images were acquired over a wavelength range from about 400-720 nm with an about 3 nm resolution. Each wavelength was assigned a custom integration time to ensure an adequate amount of time to collect the appropriate wavelength while avoiding saturation. Background images with delivery fiber blocked were taken before imaging exposed nerves, and subsequently subtracted from the images of exposed nerves. All DRS was performed with the room lights off.

Spectral and Image Processing: Three sites of adipose, skeletal muscle, and nerve tissue from each rat were used to generate average spectra of each tissue type for every rat (3 total averaged spectra/rat). Spectra for each tissue type were averaged and normalized to the peak at about 690 nm since it was consistently the highest peak in all the spectra and is one of the least absorbed wavelengths in biological tissue. Spectral markers were obtained from the averaged spectra of the six rats according to the wavelengths providing a statistically significant difference and biological justification. Intensity ratios between these wavelengths were then compared to differentiate tissue types and develop a tissue classification algorithm. Tissues were classified based on thresholding the peak ratios. Using these thresholds, maps of the tissue distribution across the DRS images were then generated on a pixel by pixel basis.

Statistical Analysis: All statistical testing was done using an unpaired t-test. Statistical testing was performed across the entire wavelength range for each tissue to determine which spectral features accounted for the best markers for tissue characterization. This test was also used to compare the peak ratios.

Results and Discussion

Figure 2A:
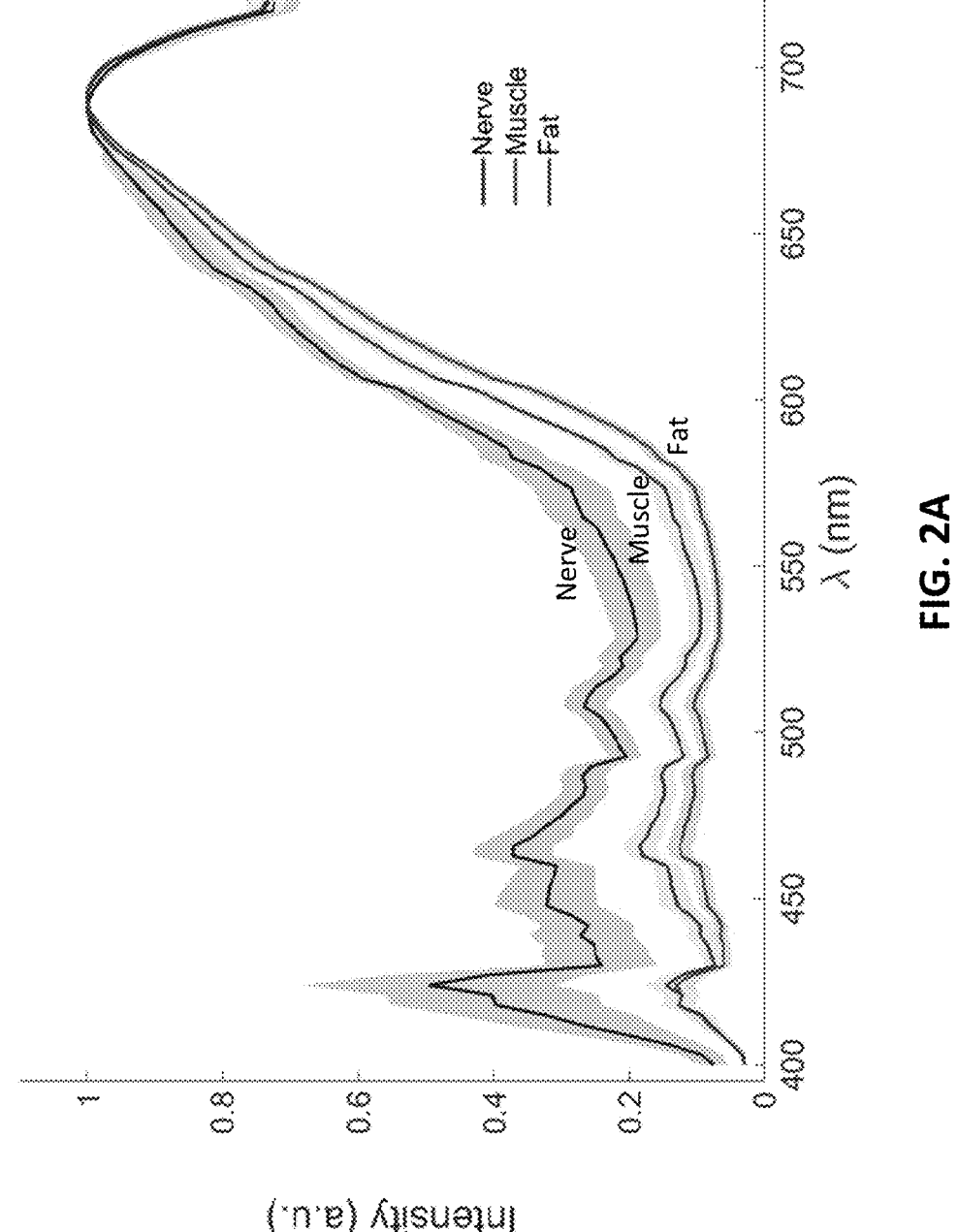
FIGS. 2A-2C show mean DR (diffuse reflectance) spectra from rat nerve, skeletal muscle, and adipose tissue, according to one embodiment of the invention.
Figure 2C:
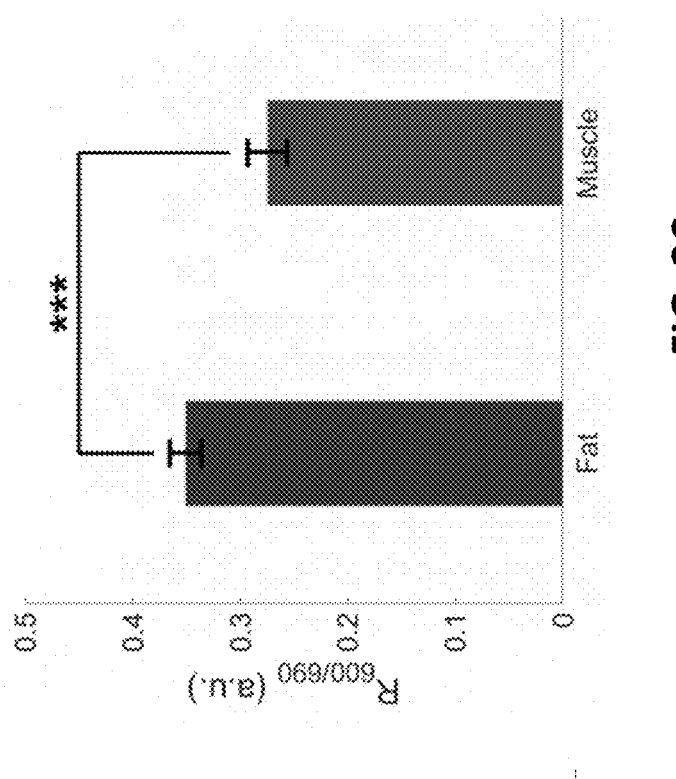
Figure 2B:
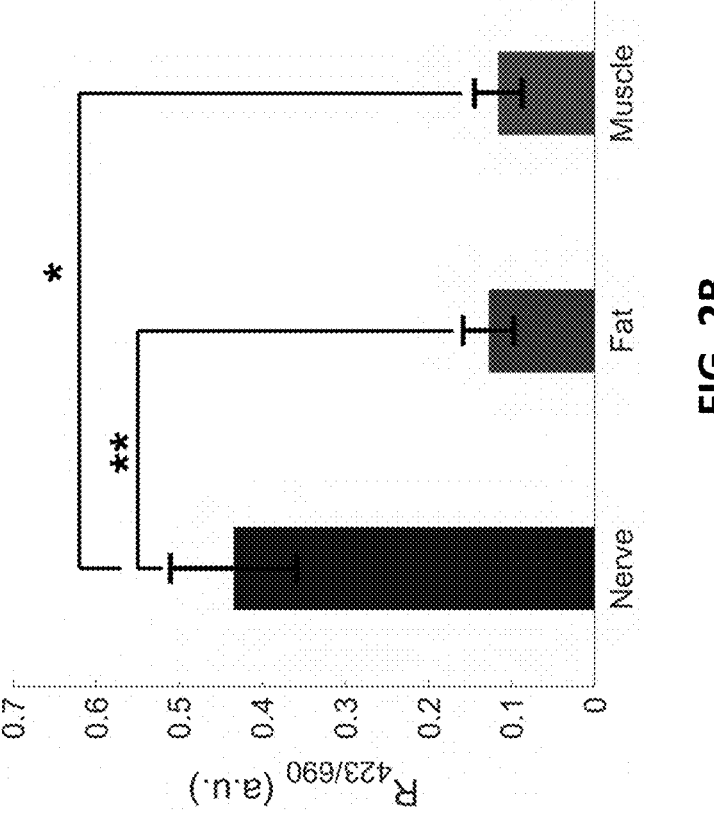

Tissue Characterization: The DR spectra acquired from the euthanized rats are shown in FIG. 2A. From the spectra, it is clear to see that the intensity at about 423 nm for nerves is substantially higher than that for either muscle or fat. After statistical analysis of the spectra, the peak at about 423 nm was identified as promising spectral marker for nerve tissue identification. Using a ratio of the intensity at 423 nm peak compared to the peak at about 690 nm of unnormalized spectra, it was found that the difference in this ratio was statistically significant for both distinguishing the nerve from the fat ($p<0.01$) and the nerve from the muscle ($p<0.05$), as shown in FIG. 2B. Similarly, to differentiate the muscle from the fat, the difference between the spectra at 600 nm was the most significant possibly owing to the fact the brown adipose tissue was present in the surgical field. Using the ratio of the intensities at 600 nm and 690 nm of the unnormalized spectra, the fat was successfully able to be distinguished from the muscle, as shown FIG. 2C ($p<0.001$). These ratios were then used to generate tissue maps across the camera's entire field of view.

Tissue Distribution Maps: Using the ratios determined above DRS spectra of each pixel of the raw, baseline corrected images were then analyzed. Thresholds were equal one standard deviation below the mean of the higher mean ratio. For instance, in distinguishing the nerve, if the 423 nm/690 nm ratio of the DR spectra is greater than about 0.36 (one standard deviation below the mean for the nerve) the pixel was classified as the nerve. If it was below that about 0.36, the 600 nm/690 nm ratio was then considered with a value greater than about 0.33 classified as the muscle and below as adipose tissue. Using this algorithm, tissue distribution maps were generated for the DRS images shown in FIGS. 3A-3B. It is shown that the submillimeter nerve was successfully classified and localized.

The objective of this exemplary example was to use DRS to distinguish nerves from surrounding tissues in a surgical field. Looking at the mean spectra acquired for nerve, muscle, and adipose tissue illustrated in FIG. 2A, nerves clearly produce enhanced DR spectra across the lower portion of a visible spectrum. Since scattering dominates in the nerve tissue in the visible range, it is expected that the nerve spectra have higher reflectance than the muscle and surprisingly adipose tissue. Moreover, since the epineurium which contains connective tissue and some blood vessels was removed, the nerve was less likely to be influenced by the absorption of blood. This is likely the reason why the 423 nm peak is more pronounced in the nerves. Though not immediately apparent at the first glance, the largest variation between the adipose and muscle tissue occurs at about 600 nm with the reflectance from the adipose tissue being higher. This can be explained by brown adipose tissue. Brown adipose tissue contains high concentrations of cytochromes that contribute to its characteristic golden color. As its colorization suggests, the brown adipose tissue has a reduction in its absorption around 590 nm which could account for this spectral marker. The presence of the brown adipose tissue, however, was not confirmed and further testing is required to determine if this is indeed the case.

The DF spectra also lacked some of the spectral features normally shown in DR tissue spectra. In particular, many of the peaks and valleys associated with blood absorption from about 550-600 nm seem to be masked in the spectra. The masking of these smaller features may be due to issues with LCTF. As shown in FIG. 1G, the spectral bandwidth of the LCTF seems to get larger with longer wavelengths and/or the percent transmission of the LCTF also increases with wavelength. More rigorous characterization of the system may be needed to recover these spectral features.

Figure 3B:
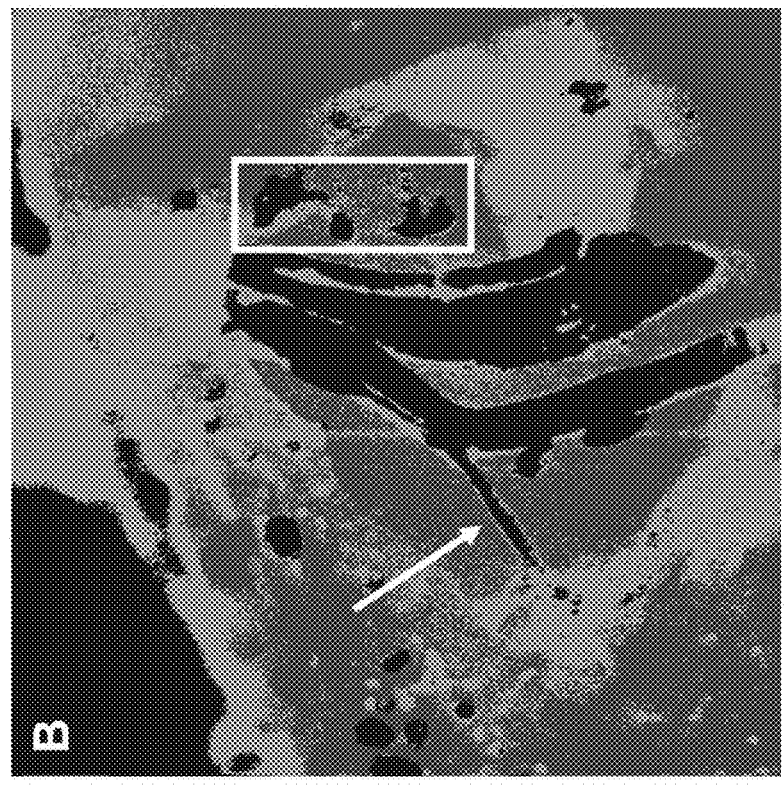
FIGS. 3A-3B show tissue distribution maps of exposed rat sciatic nerve, according to one embodiment of the invention.
Figure 3B:

According to embodiments of the invented system, nerves were able to be classified and localized in the DRS images using peak ratios. Moreover, small nerve branches (about 500 µm) were able to be detected and visualized using the 423 nm/690 nm ratio, as shown in FIG. 3B. The large area in the left-hand corner of FIG. 3B classified as nerve is skin. Since skin was not spectrally characterized in the data analysis it is not surprising that it was misclassified. Differentiating skin from nerve is also not a common challenge surgeons face as skin is pulled away from the surgical field. The upper trunk of the sciatic nerve is also misclassified as adipose tissue owing to epineurium still covering that section of the nerve. This indicates that connective tissue should also be investigated and characterized using DRS in future work. FIG. 3B also has areas of high intensity specular reflections that confound the classification algorithm. Future steps can be taken to avoid high specular reflections (collecting off-angle diffusely reflected light/use of polarization filtering). The prevalence of specular reflectance in the image is a result of attempting to have most of the uneven field in focus.

In spite of some issues in acquiring DRS images, this example presents promising evidence toward the incorporation of DRS in nerve sparring procedures. Using a ratiometric algorithm based on DF spectral features, tissue distribution maps were successfully generated and submillimeter nerves were accurately identified. Employing DRS intraoperatively could help surgeons localize nerves within the field of surgery and reduce the frequency of intraoperative nerve damage.

A critical component of DRS is to separate signals according to wavelength. As shown in FIGS. 1A-1B, for the spectral characterization, the LCTF has some spectral bleeding which increased with wavelength and broadened the peaks. The full width at half maximum (FWHM) of the LCTF filtered light increases with wavelength despite the width of the bandpass filter remaining constant. In addition, the center wavelength of the lower wavelength peaks is shifted. Evidently, the sensitive of the LCTF varies with wavelengths.

The transmission through the LCTF may also be increasing with longer wavelengths which could also explain the broadening. Lower wavelengths required longer acquisitions (about 2 s) while longer wavelengths required much shorter acquisitions (about 8 ms). In determining the acquisition times for each wavelength, extended acquisition times resulted in saturation and broader peaks. This broadening is most likely the reason some of the typical tissue spectral features are diminished. In addition, since the exposed sciatic nerve varied in depth, it was difficult to get images with multiple tissue types in focus. Working to flatten the surgical field or imaging a smaller area of interest may also lead to better results.

Figure 3A:
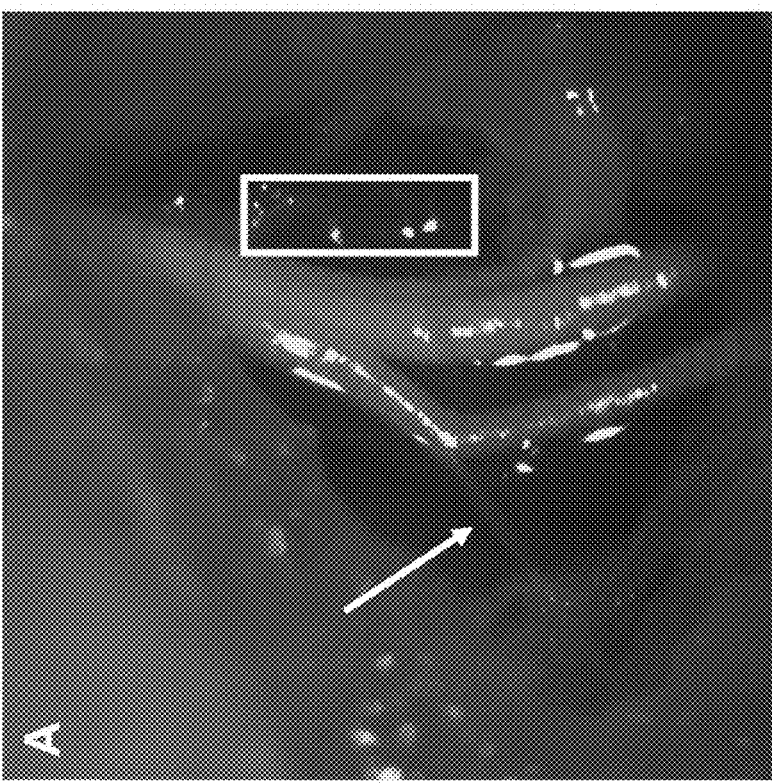

For future improvements, first and foremost, more rigorous characterization of the LCTF spectral imaging system needs to be done to ensure accurate spectra are being collected with enough sensitivity to detect smaller DRS features. Imaging live animals with the epineurium kept intact would also yield more practical results. Extending the considered wavelength range to the NIR may also provide useful information to differentiate tissues especially nerve from adipose tissue. This study also did not investigate myelinated and unmyelinated nerves. Unmyelinated nerves are often small, contain sensory axons, and are rarely identified during surgery. Future work should investigate if unmyelinated and myelinated DF spectra are distinct, and if unmyelinated can be detected apart from their myelinated counterparts. The technique presented here was also no longer effective to detect nerve once it was covered in in a thin layer of fat (FIGS. 3A-3B). Future work should focus on the depth to which nerves can be detected. Lastly, this work did not consider connective tissue which should also be characterized and investigated.

A simple t-test is insufficient to properly analyze these spectra. A more appropriate method would be ordinary least squares regression model which can estimate the spectral contribution from each tissue type at a given pixel. In this way, a pixel that may not be entirely composed of just adipose tissue can also partially be assigned to muscle as well. Principle component analysis may also be a valuable analytic tool to tease out spectral markers. The spectral markers used to distinguish tissue types should also be grounded in the biological and optical properties of the respective tissues.

In the non-limiting exemplary examples, the apparatus and method disclosed herein are applied for identifying and/or visualizing nerves. However, it should be appreciated to one skilled in the art that the apparatus and method disclosed herein are not limited to just identifying and/or visualizing nerves, but can be applied in other instances connective tissue, fat, muscle, blood vessels, etc., as well.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

[1]. Campbell, W. W. Evaluation and management of peripheral nerve injury. *Clin. Neurophysiol.* 119, 1951-1965 (2008).

[2]. Seddon, H. J. Three Types of Nerve injury. *Brain* 66, 238-288 (1943).

[3]. Stanford, J. L. et al. Urinary and Sexual Function After Radical Prostatectomy for Clinically Localized Prostate Cancer. *JAMA* 283, 354 (2000).

[4]. Delank, K. S. et al. Iatrogenic paraplegia in spinal surgery. *Arch. Orthop. Trauma Surg.* 125, 33-41 (2005).

[5]. Kaylie, D. M., Gilbert, E., Horgan, M. A., Delashaw, J. B. & McMenomey, S. O. Acoustic Neuroma Surgery Outcomes. *Otol. Neurotol.* 22, 686-689 (2001).

[6]. Abadin, S. S., Kaplan, E. L. & Angelos, P. Malpractice litigation after thyroid surgery: The role of recurrent laryngeal nerve injuries, 1989-2009. *Surgery* 148, 718-723 (2010).

[7]. Morris, L. G. T., Ziff, D. J. S. & DeLacure, M. D. Malpractice Litigation After Surgical Injury of the Spinal Accessory Nerve. *Arch. Otolaryngol. Neck Surg.* 134, 102 (2008).

[8]. Schneider, R. et al. Continuous intraoperative vagus nerve stimulation for identification of imminent recurrent laryngeal nerve injury. *Head Neck* 35, 1591-1598 (2013).

[9]. Schneider, R. et al. Continuous intraoperative neural monitoring of the recurrent nerves in thyroid surgery: a quantum leap in technology. *Gland Surg.* 5, 607-616 (2016).

[10]. Whitney, M. A. et al. Fluorescent peptides highlight peripheral nerves during surgery in mice. *Nat. Biotechnol.* 29, 352-356 (2011).

[11]. Lewis, S., Price, A., . . . K. W.-C. D. & 2015, undefined. Ultrasound guidance for upper and lower limb blocks. *cochranehbrary.com*

[12]. Poggio, D. et al. Correlation Between Visual Inspection and Ultrasonography to Identify the Distal Branches of the Superficial Peroneal Nerve: A Cadaveric Study. *J. Foot Ankle Surg.* 55, 492-495 (2016).

[13]. Lee, F. L., Singh, H., Nazarian, L. N. & Ratliff, J. K. "High-resolution ultrasonography in the diagnosis and intraoperative management of peripheral nerve lesions. *J. Neurosurg.* 114, 206-211 (2011).

[14]. Koenig, R. W. et al. Intraoperative high-resolution ultrasound: a new technique in the management of peripheral nerve disorders. *J. Neurosurg.* 114, 514-521 (2011).

[15]. Hussain, T., Nguyen, L. T., Whitney, M., Hasselmann, J. & Nguyen, Q. T. Improved facial nerve identification during parotidectomy with fluorescently labeled peptide. *Laryngoscope* 126, 2711-2717 (2016).

[16]. Chin, K. W. T. K. et al. Evaluation of collimated polarized light imaging for real-time intraoperative selective nerve identification in the human hand. *Biomed. Opt. Express* 8, 4122 (2017).

[17]. Boppart, S. A. Optical coherence tomography: Technology and applications for neuroimaging. *Psychophysiology* 40, 529-541 (2003).

[18]. Boehm, J., Scheidl, E., Bereczki, D., Schelle, T. & Arányi, Z. High-Resolution Ultrasonography of Peripheral Nerves: Measurements on 14 Nerve Segments in 56 Healthy Subjects and Reliability Assessments. *Ultraschall der Medizin—Eur. J. Ultrasound* 35, 459-467 (2014).

[19]. Kosaka, N., Ogawa, M., Choyke, P. L. & Kobayashi, H. Clinical implications of near-infrared fluorescence imaging in cancer. *Futur. Oncol.* 5, 1501-1511 (2009).

[20]. Finke, M. et al. Automatic scanning of large tissue areas in neurosurgery using optical coherence tomography. *Int. J. Med. Robot. Comput. Assist. Surg.* 8, 327-336 (2012).

[21]. Zonios, G. et al. Diffuse reflectance spectroscopy of human adenomatous colon polyps in vivo. *Appl. Opt.* 38, 6628 (1999).

[22]. Garcia-Uribe, A. et al. In vivo diagnosis of melanoma and nonmelanoma skin cancer using oblique incidence diffuse reflectance spectrometry. *Cancer Res.* 72, 2738-45 (2012).

[23]. Mallia, R. et al. Oxygenated hemoglobin diffuse reflectance ratio for in vivo detection of oral pre-cancer. J. Biomed. Opt. 13, 041306 (2008).

[24]. Toms, S. A. et al. Intraoperative Optical Spectroscopy Identifies Infiltrating Glioma Margins with High Sensitivity. *Oper. Neurosurg.* 57, 382-391 (2005).

[25]. Joel, C. D. & Ball, *E. G. The Electron Transmitter System of Brown Adipose Tissue*. Harvey Lectures* 1, (Lehninger, A. L, 1962).

[26]. Gebhart, S. C., Lin, W. C. & Mahadevan-Jansen, A. In vitro determination of normal and neoplastic human brain tissue optical properties using inverse adding-doubling. *Phys. Med. Biol.* 51, 2011-2027 (2006).

[27]. Schols, R. M. et al. Differentiation between nerve and adipose tissue using wide-band (350-1,830 nm) in vivo diffuse reflectance spectroscopy. *Lasers Surg. Med.* 46, 538-545 (2014).

[28]. Langhout, G. C. et al. In vivo nerve identification in head and neck surgery using diffuse reflectance spectroscopy. *Laryngoscope Investig. Otolaryngol.* 3, 349-355 (2018).

[29]. Minamikawa, T. et al. Label-free detection of peripheral nerve tissues against adjacent tissues by spontaneous Raman microspectroscopy. *Histochem. Cell Biol.* 139, 181-193

What is claimed is:

1. An apparatus for label-free visualization of a target of interest of a living subject, comprising:
a light source configured to emit light;
an imaging head configured to acquire a polarized diffuse reflectance spectroscopy (DRS) image from the target of interest;
an optical waveguide configured to polarize light emitted from the light source and operably arranged between the light source and the target of interest;
a tunable filter arranged at the imaging head; and
a controller configured to:
control the imaging head and to process the polarized DRS image;
identify a normalization spectral marker corresponding to a wavelength least absorbed by the target of interest;
identify at least one tissue spectral marker corresponding to a wavelength of statistically significant reflectance intensity;
normalize the polarized DRS image based on the normalization spectral marker; and
identify one or more reflectance intensity ratios between the normalization spectral marker and the at least one tissue spectral marker present in the normalized polarized DRS image;
identify one or more tissue types visualized in the target of interest based at least on a threshold associated with the one or more reflectance intensity ratios.

2. The apparatus of claim 1, wherein the controller is configured to:
cause the imaging head to acquire a background image where the light source does not emit a beam of light; and
process the polarized DRS image based on the background image by subtracting the background image from the polarized DRS image.

3. The apparatus of claim 1, wherein
the normalization spectral marker has a wavelength between about 575 nm to about 700 nm; and
the at least one tissue spectral marker has a wavelength between about 410 nm to about 460 nm or between about 580 nm to about 620 nm.

4. The apparatus of claim 1, wherein
the normalization spectral marker has a wavelength between about 680 nm to about 700 nm; and
the at least one tissue spectral marker has a wavelength between about 410 nm to about 440 nm or between about 590 nm to about 610 nm.

5. The apparatus of claim 1, wherein the controller is further configured to:
identify a tissue type in the polarized DRS image; and
generate a tissue type distribution based on the identified tissue type.

6. The apparatus of claim 1, wherein the controller is further configured to:
identify a tissue type in the polarized DRS image; and
generate a pixel-by-pixel tissue type distribution based on the identified tissue type.

7. The apparatus of claim 6, further comprising a display for displaying the pixel-by-pixel tissue type distribution, projecting the pixel-by-pixel tissue type distribution onto an intraoperative field of view, or a combination thereof.

8. The apparatus of claim 1, wherein the light source is a broadband light source that emits light at a wavelength of about 100 to about 1200 nm.

9. The apparatus of claim 1, wherein the optical waveguide comprises:
one or more wave plates further comprising a fixed axis of transmission or a variable axis of transmission, or both,
wherein the one or more wave plates is configured to produce light with a linear polarization state, an elliptical polarization state, a circular polarization state, or a combination thereof.

10. The apparatus of claim 1, wherein the optical waveguide comprises:
one or more optical fibers further comprising at least one of a fixed axis of transmission, a variable axis of transmission, or both,
wherein the one or more optical fibers are configured to produce light with a linear polarization state, an elliptical polarization state, a circular polarization state, or combinations thereof.

11. The apparatus of claim 1, wherein the imaging head comprises:
a detector disposed in a top portion of the imaging head for acquiring the polarized DRS image;
the tunable filter positioned in a bottom portion of the imaging head in an optical path for collecting light from the target of interest; and
a lens positioned between the tunable filter and the detector in the optical path for focusing the collected light to the detector.

12. The apparatus of claim 11, wherein the detector comprises at least one camera selected from at least one chargecoupled device (CCD) camera, at least one complementary metal oxide semiconductor (CMOS) camera, at least one photosensor array, at least one infrared camera, at least one near-infrared (NIR) camera, or a combination thereof.

13. The apparatus of claim 11, wherein the tunable filter comprises:

an optical filter that uses electronically controlled liquid crystal (LC) elements to transmit a selectable wavelength of light and exclude others, with fixed polarizations, variable polarizations, or a combination thereof; or a dispersion-based filter configured to produce a spatially distributed continuous wavelength spectrum capable of being operably sampled for individual wavelengths, bands of wavelengths, a full spectrum of wavelengths, or combinations thereof; or variable spectral bandpass filters, variable polarization filters, or a combination thereof.

14. The apparatus of claim 11, wherein the light source is operably modulated by a lock-in scheme or a transistor-transistor logic (TTL) trigger for providing a trigger to sequence data collection, initiate data collection, or a combination thereof for enabling operations of the detector in normal lighting conditions, and/or external lighting conditions, or a combination thereof, including room lights.

15. The apparatus of claim 11, wherein the imaging head further comprises one or more lenses positioned between the target of the interest and the tunable filter for focusing the light from the target of interest to the tunable filter.

16. The apparatus of claim 1 wherein the controller is further configured to provide, based on the polarized diffuse reflectance spectroscopy (DRS) image, an aural or tactile nerve predetermined proximity indication.

\*   \*   \*   \*   \*